United States Patent [19]

Dakubu

[11] Patent Number: 4,968,631

[45] Date of Patent: Nov. 6, 1990

[54] METHOD FOR DETECTING AMINES AND ALDEHYDES USING LANTHANIDE CHELATE FLUOROPHORES BASED ON DIHYDROPYRIDINE CONDENSATION PRODUCTS

[75] Inventor: Salifu Dakubu, Winchester, Mass.

[73] Assignee: Golight, Inc., Winchester, Mass.

[21] Appl. No.: 414,959

[22] Filed: Sep. 29, 1989

Related U.S. Application Data

[62] Division of Ser. No. 243,303, filed as PCT US87/00206 on Jan. 30, 1987 published as WO87/04716 on Aug. 13, 1987, Pat. No. 4,891,075.

[30] Foreign Application Priority Data

Jan. 30, 1986 [GB] United Kingdom ............... 8602304

[51] Int. Cl.$^5$ .................... G01N 21/17; G01N 21/75
[52] U.S. Cl. .................................. 436/111; 436/82; 436/86; 436/96; 436/128; 436/172
[58] Field of Search .................. 436/82, 86, 89, 90, 436/96, 111, 128, 130, 172

[56] References Cited

U.S. PATENT DOCUMENTS

| | | | |
|---|---|---|---|
| 3,484,606 | 12/1969 | Masi | 250/367 |
| 3,546,460 | 12/1970 | Lally | 250/483.1 |
| 3,956,341 | 5/1976 | Loev . | |
| 4,058,732 | 11/1977 | Wieder . | |
| 4,190,465 | 2/1980 | Boling . | |
| 4,352,751 | 2/1986 | Wieder et al. . | |
| 4,374,120 | 2/1983 | Soini et al. . | |
| 4,492,778 | 1/1985 | Claussen et al. . | |
| 4,572,803 | 2/1986 | Yamazoe et al. . | |
| 4,584,428 | 4/1986 | Garlick | 136/257 |
| 4,605,849 | 8/1986 | Kliem et al. | 250/216 |
| 4,629,821 | 12/1986 | Bronstein-Bonte et al. | 136/257 |
| 4,682,019 | 7/1987 | Nakatsui et al. | 250/211 R |

FOREIGN PATENT DOCUMENTS 195413 9/1986 European Pat. Off. .
8601604 3/1986 PCT Int'l Appl. .
350461 1/1961 Switzerland .

OTHER PUBLICATIONS

Nash, The Biochemical Journal, vol. 55, pp. 416–421, 1953.

The Journal of Chemical Physics, vol. 10, issued Apr. 1942 (New York, N.Y.), S. I. Wiessman, "Intramolecular Energy Transfer: The Fluorescence of Complexes of Europium", see pp. 214–217, especially p. 216, Table II.

Primary Examiner—Robert J. Hill, Jr.
Attorney, Agent, or Firm—Lorusso & Loud

[57] ABSTRACT

Fluorescent lanthanide chelates are formed by reacting a β-diketone, an aldehyde, and an amine to produce a dihydropyridine condensation product which is then chelated with a lanthanide metal ion. These fluorescent chelates are made into wavelength-shifting devices by physically supporting the chelates on a polymer. Such wavelength-shifting devices can be optically coupled to a photoelectric cell to increase the portion of the solar spectrum available to the cell for conversion into electricity. Furthermore, the reaction producing the fluorescent lanthanide chelates is used to detect amines or aldehydes in a sample.

4 Claims, 5 Drawing Sheets

| LANTHANIDE | TRANSITION | EMISSION (nm) |
|---|---|---|
| Eu | $^5D_0 - {}^7F_2$ | 615 |
| Tb | $^5D_4 - {}^7F_6$ | 490 |
| | $^5D_4 - {}^7F_2$ | 650 |
| Sm | $^4G_{5/2} - {}^6F_{9/2}$ | 1150 |
| | $^4G_{5/2} - {}^6H_{9/2}$ | 640 |
| Dy | $^4F_{9/2} - {}^6H_{13/2}$ | 580 |
| | $^4F_{9/2} - {}^6H_{5/2}$ | 940 |

METHOD FOR DETECTING AMINES AND ALDEHYDES USING LANTHANIDE CHELATE FLUOROPHORES BASED ON DIHYDROPYRIDINE CONDENSATION PRODUCTS

This is a divisional of copending application Ser. No. 243,303, filed as PCT US89/00206 on Jan. 30, 1987 published as WO87/04716 on Aug. 13, 1987, now U.S. Pat. No. 4,891,075.

BACKGROUND OF THE INVENTION

This invention relates to useful applications of the formation of a dihydropyridine condensation product formed by the reaction of a $\beta$-diketone, an aldehyde and an amine. More particularly it relates to a wavelength shifting device which permits a photovoltaic cell to collect energy from the energy-rich portion of the solar spectrum and to sensitive methods of detecting amines and aldehydes. The invention exploits the long-lived fluorescence and large Stoke's shift associated with the lanthanide ion chelate fluorophores that can be made with the condensation products.

That part of the solar spectrum below 450 nm is poorly or not at all available for conversion to electricity by photovoltaic cells. Furthermore, this part of the solar spectrum is very rich in energy at the surface of the earth and even more so extraterrestrially. These facts are well documented in "Sunlight to Electricity: Prospects for Solar Conversion by Photovoltaics" Joseph A. Merrigan, MIT Press, Cambridge, Mass. (1975). Attempts have been made to reduce the problem using luminescent solar collectors (LSC) which are dye-doped plastics or glass plates. A type of dye advocated is a weak metal chelate. For example, M.S. Cook and A.J. Thomson in "Chemistry in Britain" (Oct. 1984, p.914-917) advocate the use of ruthenium (II) complexes with 2-2'-bipyridine or 1-10-phenanthroline. They report, however, that these materials do not have long term photostability. This problem stems from the low stability that would be associated with the use of a metal to bidentate chelate even in 1:3 ratio in dilute solution in the plastic or glass. What is required is a fluorophore with a large Stoke's shift which is also able to remain in long term photostability.

It is known from U.S. Pat. No. 3,956,341 and International Patent Application PCT/GB85/00337 that an aldehyde ($R^1$—CHO), an amine ($R^2$—$NH_2$) and a $\beta$-diketone ($R^3COCH_2COR^4$) (with $R^1$, $R^2$, $R^3$ and $R^4$ being arbitrary organic radicals and $R^1$ and $R^2$ optionally being hydrogen) react to form a dihydropyridine condensation product as illustrated in FIG. 1. The reaction is preferrably carried out at a mildly acidic pH (5.5–6.5) and a mildly elevated temperature (30°–80° C). It is dependent only on the basic structure of the aldehyde, amine and $\beta$-diketone and not on the nature of the substituents $R^1$ to $R^4$ so that it can be used with a wide variety of aldehydes, amines and $\beta$-diketones. Examples of $\beta$-diketones are trifluoroacetylacetone, thenoyltrifluoroacetone and benzoyl and alpha- and beta-naphthoyl trifluoroacetone as well as the $\beta$-diketones mentioned in U.S. Pat. No. 4,374,120. Other $\beta$-diketones that might be employed are carboxy-modified versions of the above mentioned $\beta$-diketones.

The dihydropyridine condensation product, according to Nash (T. Biochem. J. 55, 1953, p.416–421), has the capability to form an enol at the 4 position and probably holds a metal ion by chelation at that site. When the chelated metal is a lanthanide metal ion, especially Eu(III) or Tb(III) but also Sm(III) or Dy(III), the metal ion and the condensation product exist as an acceptor-donor pair, so that the condensation product acts as a chelating chromophore, absorbing excitation radiation at its characteristic absorption peak(s) and by energy transfer inducing the resonance fluorescence of the lanthanide metal ion. These fluorescence properties are recognized in International Patent Application PCT/GB85,/00337 and used to produce lanthanide ion fluorescent labels to be used in fluoroimmunoassays. The valuable properties of the chelating condensation products can be utilized in several ways and the present invention is concerned with the utilization.

Any chelates with suitable absorption and donor properties as those described for the condensation product and able to form kinetically stable 1:1 chelates with lanthanide metal ions would serve a similar purpose of wavelength conversion. A class of such chelates and methods for making them are disclosed in European Patent Application No. 0,195,413. Those with good quantum efficiencies for the fluorescence of Eu(III), Sm(III) and Dy(III) are to be preferred as the principal emission bands, as shown in FIG. 3, of these ions are more available to the commonest sort of photovoltaic cells. Except for CdS cells, the absorption edges for most other popular photovoltaic materials lie beyond 800 nm.

In addition to the work that has been done on photovoltaic cells and dihydropyridine condensation products, fluorometric methods have been used to detect chemical substances. The sensitivity of these detection systems is inhibited by the high background fluorescence associated with most organic substances. A highly sensitive analytical procedure for the determination of formaldehyde, for example, is useful in the study of biological systems and air pollution. Many biological substances such as sugars, hydroxamino acids, methanol, formic acid etc. are determined by first converting them to formaldehyde by oxidation or reduction. Also, the detection and estimation of amines, especially in amino acids and proteins, are important in biochemical studies. In chromatography it is important to be able to detect small quantities rapidly. The use of chelates of lanthanide ions as fluorescent labels in the determination of aldehydes and amines offers a great improvement in signal to noise ratios over previously used fluorophores.

SUMMARY OF THE INVENTION

In accordance with the present invention, it has been discovered that photovoltaic cells, when optically coupled to a wavelength-shifting device comprising a polymer containing a lanthanide metal ion chelated to a dihYdropYridine condensation product, can utilize energy from the energy-rich portion of the solar spectrum. This portion of the solar spectrum was previously unavailable to photovoltaic cells. Accordingly, the present invention utilizes a dihydropyridine condensation product which is chelated to a lanthanide ion in a polymer as a wavelength-shifting device which can be coupled to a photovoltaic cell. The condensation product absorbs a significant level of energy and transfers the energy to the lanthanide ion. The lanthanide ion then emits or fluoresces at a longer wavelength. Present photovoltaic cells are only able to collect energy from these longer wavelengths. By coupling this chelated condensation product to a solar cell, energy from the low-wavelength portion of the solar spectrum is finally available for conversion to electricity.

The present invention also uses the components of the dihydropyridine condensation product chelated to a lanthanide ion to detect for amines and aldehydes. The dihydropyridine condensation product is composed of a β-diketone, an aldehyde and an amine. It exploits the long-lived fluorescence and large Stoke's shift associated with the lanthanide ion chelate fluorophores that can be made with the condensation products.

It is therefore a object of the present invention to provide a photo-converting device which absorbs energy from the energy-rich portion of the solar spectrum (280–460 nm).

It is another object of the present invention to provide a coating for present photovoltaic cells which absorbs energy from the energy-rich portion of the solar spectrum (280–460 nm) and emits energy in a form (540 nm and beyond) which is better available to present photovoltaic cells.

It is a further object of the present invention to provide a coating for present photovoltaic cells which absorbs energy from the energy-rich portion of the solar spectrum (280–460 nm) and emits energy in a form (540 nm and beyond) which is better available to present photovoltaic cells and the fluorophore has long term photostability.

It is another object of the present invention to increase the sensitivity or signal to noise ratio over previously used fluorophores.

DESCRIPTION OF THE PREFERRED EMBODIMENTS

Figure 1:
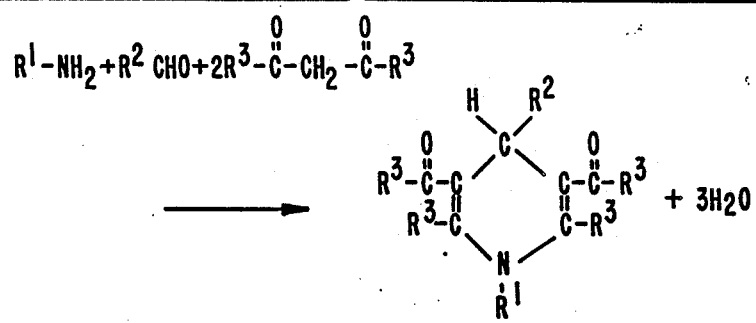
FIG. 1 is an illustration of the dihydropyridine condensation reaction.

At the outset, the invention is described in its broadest overall aspects with a more detailed description following. The properties of the condensation product are utilized to produce a wavelength-shifting material. Such a material comprises the chelation product of a fluorescing lanthanide metal ion and a solid forming dihydropyridine condensation product of an $NH_2$-bearing reagent, a β-diketone-bearing reagent and an aldehyde-bearing reagent, one of which reagents forms part of a polymer. The material absorbs energy at the excitation band absorption maxima of the dihydropyridine condensation product and emits energy at the characteristic wavelength corresponding to the metal ions chelated.

Conveniently, the $NH_2$-bearing reagent is a polymer. Polyethyleneimine is an example of such a polymer. Alternatively the aldehyde-bearing reagent may be a polymer. If desired, pre-existing polymers used as structural parts of conventional photovoltaic cells may be modified by incorporation of amine or aldehyde or β-diketone groups prior to reaction with the other reagents to form the dihydropyridine condensation product. Such a polymer is the polyimide used with CdS photovoltaic cells as described by S.A. Merrigan in "Sunlight to Electricity: Prospects for Solar Conversion by Photovoltaics." MIT Press, Cambridge, Mass. (1975).

The wavelength-shifting material may be dispersed in a transparent material such as glass or a plastic material, for example polystyrene or polypropylene or some co-polymer suitable for use with photovoltaic cells, if it does not itself already form a transparent polymer useful for such purposes. The resulting product may be placed on one face of a silicon or other photovoltaic cell or as a part of a luminescent solar collector device (LSC). Such a device will absorb solar energy at the wavelengths of 280–460 nm, which is the energy-rich region of the solar spectrum. This energy range is generally not available to conventional photovoltaic devices. The device will emit energy in the region of 540–650 nm and beyond, which is a range that is better available to silicon or other photovoltaic cell or device. Further details of the construction and arrangement of an LSC device are given in an article by M.S. Cook and A.J. Thomson. Similar constructions can be used with the characterizing condensation products of this invention.

Any chelates with suitable absorption and donor properties as those described for the condensation product and able to form kinetically stable 1:1 chelates with lanthanide metal ions would serve a similar purpose of wavelength conversion. A class of such chelates and methods for making them are disclosed in European Patent Application No. 0,195,413. Those with good quantum efficiencies for the fluorescence of Eu(III), Sm(III), and Dy(III) are to be preferred as the principal emission bands of these ions are more available to the commonest sort of photovoltaic cells. Except for CdS cells, the absorption edges for most other popular photovoltaic materials lie beyond 800 nm.

The formation of the condensation product is used to present a metal in a convenient form, possibly having new electronic, electrical or chemical properties. Because it is possible to use a wide variety of amines and aldehydes in the condensation reaction, the choice of these materials can be dictated by a desire to chelate any desired metal. When the metal-bearing condensation product is formed in a polymer or dispersed in a polymer, the metal is present in a kinetically stable state as a result of its strong chelation. Thus it is possible to provide a thin film of one or more metals by this means.

Figure 2:
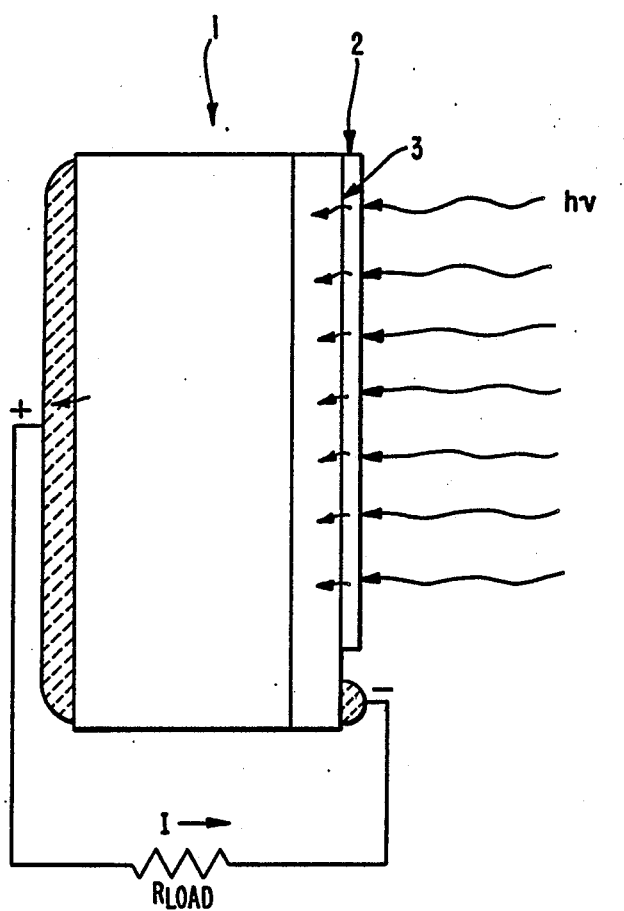
FIG. 2 is a schematic diagram of the photo-electric device with a coating containing a lanthanide metal ion chelated to a dihydropyridine condensation product.
Figure 5:
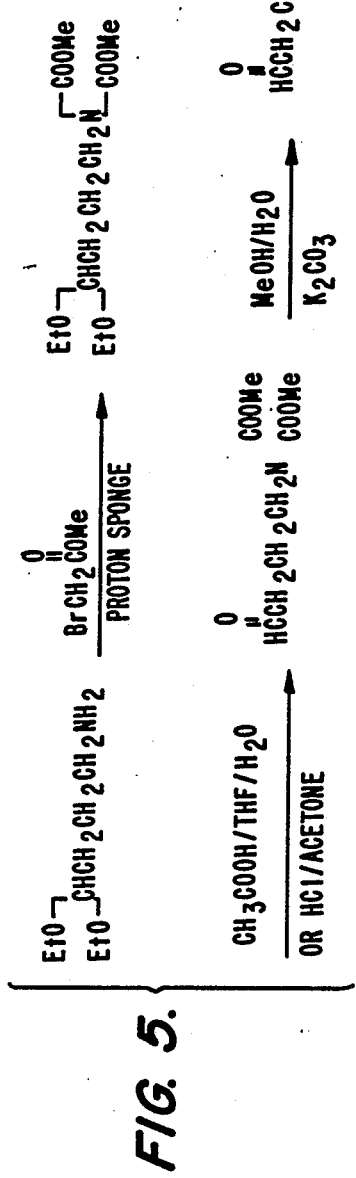
FIG. 5 illustrates an example of a chelating aldehyde and a method for producing it.
Figure 6:
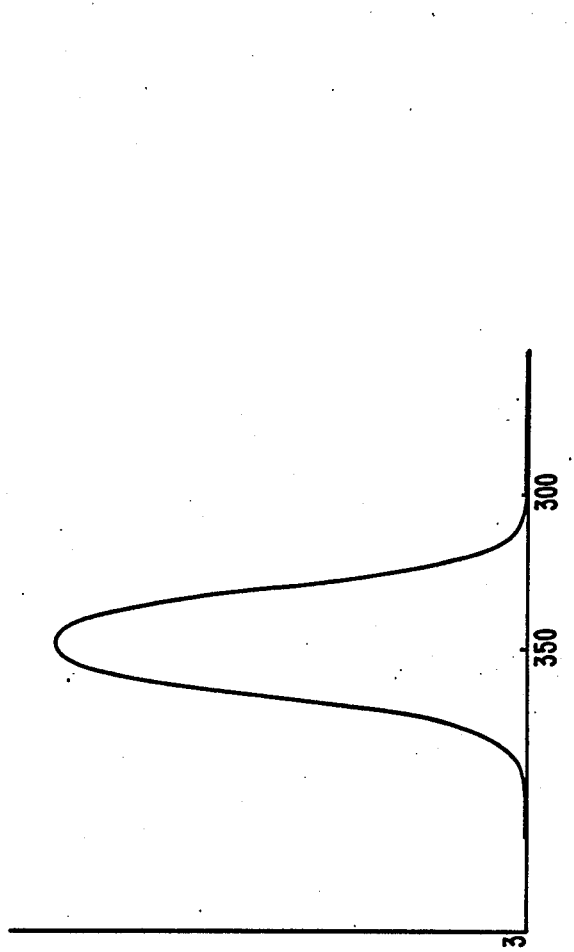
FIG. 6 illustrates the excitation spectrum of the β-diketone shown in FIG. 4 chelating Eu(III) with an emission of 613 nm.
Figure 8:
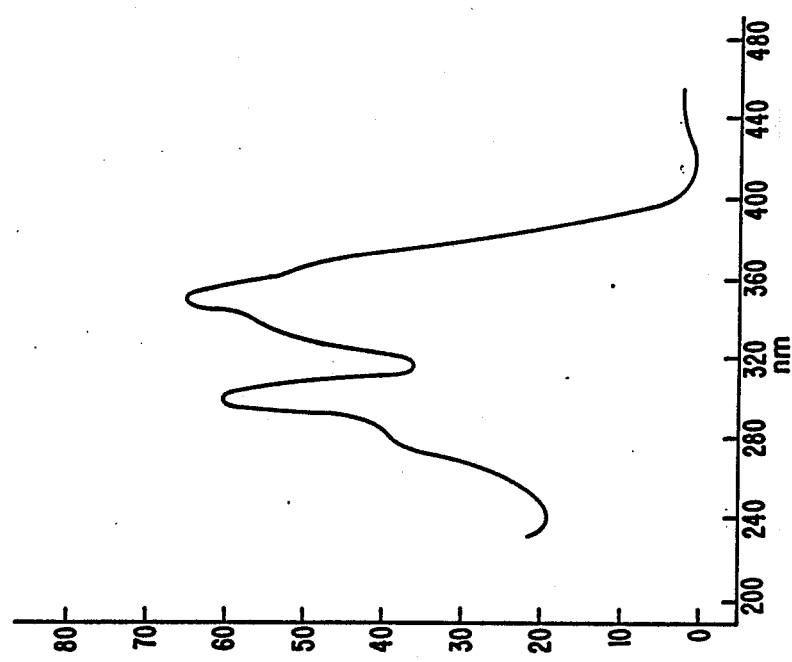
FIG. 8 illustrates the excitation spectrum of multiple covalently linked β-diketone of FIG. 4 chelating Eu-(III).
Figure 7:
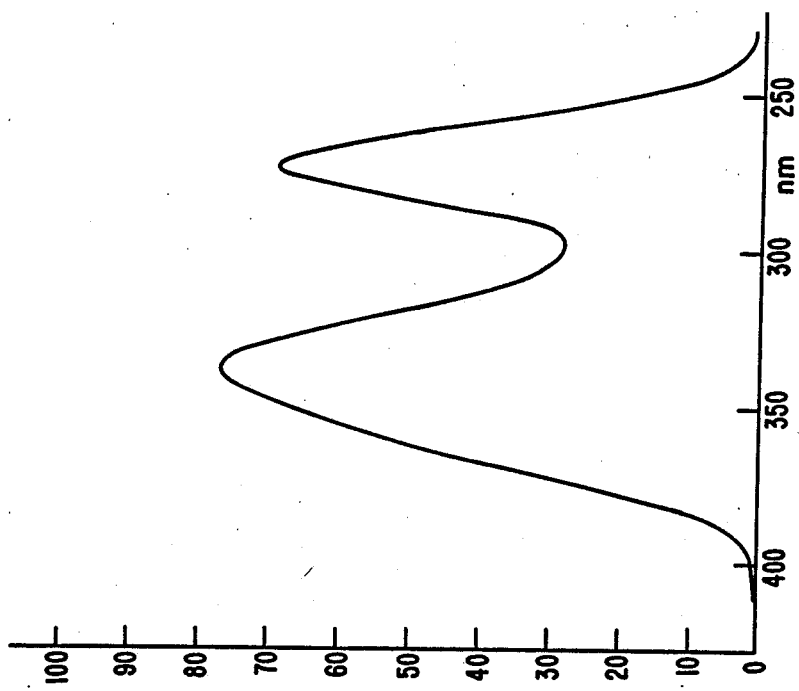
FIG. 7 illustrates the excitation spectrum of the dihydropyridine condensation product of the β-diketone of FIG. 4 and the chelating aldehyde of FIG. 5 with a mouse monoclonal antibody against carcinoembryonic antigen (CEA) as an example both of an amine and a polymer. Eu(III) has an emission of 613 nm.
Figure 10:
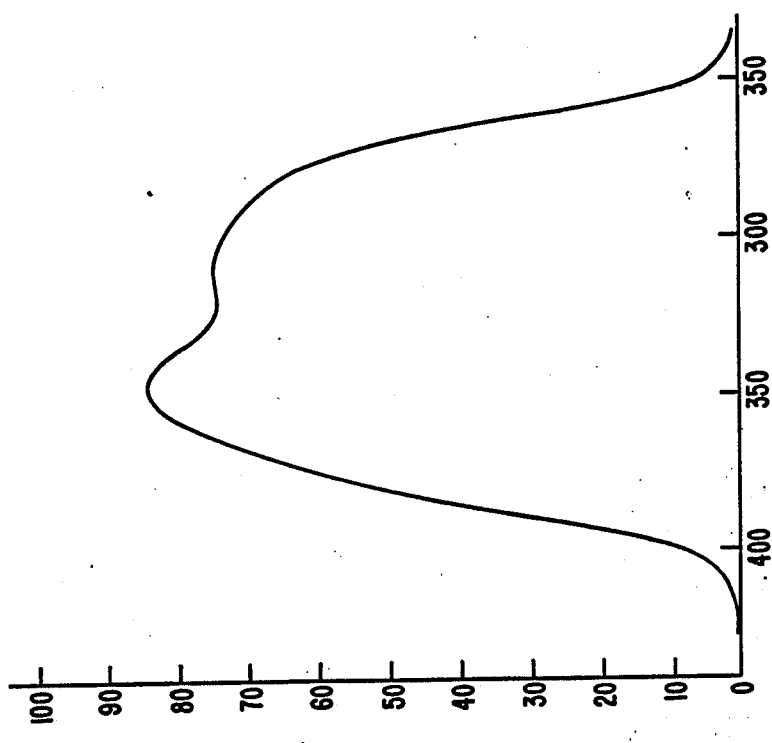
FIG. 10 illustrates the excitation spectrum of the condensation product of the multiple-covalently linked β-diketone, formaldehyde and the monoclonal anti CEA. Eu(III) has an emission of 613 nm.
Figure 9:
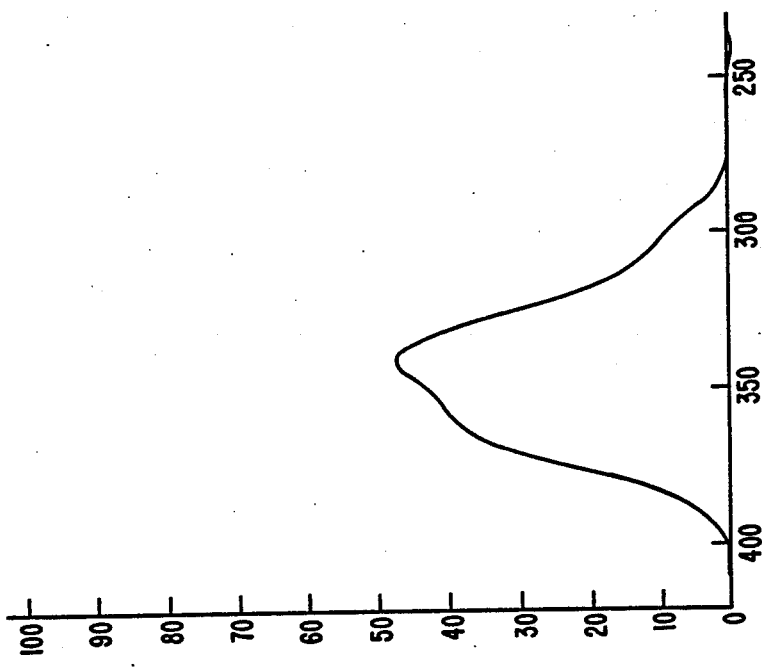
FIG. 9 illustrates the excitation spectrum of the condensation product of the multiple-covalently linked β-diketone, the chelating aldehyde of FIG. 5 and the monoclonal anti CEA. Eu(III) has an emission of 613 nm.

The photoelectric device, illustrated in FIG. 2, consists of a photovoltaic cell (1) with a coated polymer (2) on its face. The coated polymer (2) is a material with long term photostability. The coated polymer (2) is a polymer of a dihydropyridine condensation product chelated with a lanthanide metal ion. The coated polymer (2) is composed of the reactants illustrated in FIG. 1 and reacted under the conditions previously mentioned. A suggested β-diketone for this purpose is the modified thenoyltrifluoroacetone illustrated in FIG. 4 which increases solubility and increases the stability constant for chelating lanthanide metal ion in the final dihydropyridine compound. This β-diketone provides extra coordination ability. An example of a chelating aldehyde and a method for producing it is illustrated in FIG. 5. The chelated lanthanide ions which are chelated to the condensation product emit energy within the range most accessible to the photovoltaic cell and are listed in FIG. 3. The coating absorbs energy from the energy-rich portion of the solar spectrum (280–460 nm) as illustrated in FIG. 7. The coated polymer is then absorbed on a transparent material (3) and placed on the face of the photovoltaic cell. The device as shown in FIG. 2 in its entirety is subjected to sunlight and converts energy into electricity.

The following reagents were used in the following example which is presented for illustrative purposes only and is not intended to limit the scope of the invention.

(1) A commercially available polymer which possesses an amino group, mouse monoclonal antibody against carcinoembryonic antigen (CEA), is in a solution containing approximately 10 mg/ml.

(2) A 1:1000 dilution of a aldehyde solution originally 37–40% w/v in the aldehyde of FIG. 5, thus now having a concentration of about $1.4 \times 10^{-3}$ moles/liter.

Figures 3, 4:
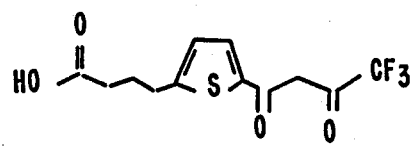
FIG. 3 shows the principal emission lines of some of the lanthanide ions of interest.
FIG. 4 illustrates the slightly modified molecule thenoyltrifluoroacetone which provides good solubility and extra coordination ability.

(3) A stock solution of the modified β-diketone illustrated in FIG. 4 in methanol at a concentration of 160 mM.

EXAMPLE

The coating was manufactured with 400 μl of the mouse monoclonal antibody solution ($2.7 \times 10^{-8}$ mole of antibody) were incubated at 37° C. for 1 hour with 200 μl of the diluted aldehyde solution ($2.7 \times 10^{-7}$ mole of aldehyde) and 4 μl of the β-diketone solution ($5.4 \times 10^{-7}$ mole of β-diketone) in an acetate buffer (0.2 M) at a pH of 5.7. The reaction product was dialysed initially against the acetate buffer to remove unreacted small molecules then against the acetate buffer containing Eu(III) ions at $10^{-7}$ M concentration to form the chelation product (the fluorophore) and finally against the acetate buffer to remove excess Eu(III).

The dihydropyridine condensation product chelated to Eu(III) was coated onto a thin, transparent polystyrene sheet by physical adsorption. The coated polystyrene sheet was place on the face of a Radio Shack model photovoltaic cell. The photo-conducting device was exposed to sunlight. The electrical current was measured and compared to the electrical output monitored from the Radio Shack model with only the polystyrene sheet on its face and under the same conditions.

According to a second aspect of the invention, the formation of the dihydropyridine condensation product is used as a means of detecting the presence of amines or aldehydes. The detection system is used especially in high performance liquid chromatography (HPLC). Thus, a process for detecting the presence of an amine in a material stream comprises contacting the material stream with a β-diketone and an aldehyde with chelation functionality carrying a lanthanide metal ion by chelation and detecting the presence or absence of fluorescence at the excitation maximum of the dihydropyridine condensation product. Similarly, a process for detecting the presence of an aldehyde in a material stream comprises contacting the material stream with a β-diketone and an amine carrying a lanthanide metal ion by chelation and detecting the presence or absence of the fluorescence at an appropriate excitation maximum of the dihYdropYridine condensation product. The chelate attached to the amine could have a high stability constant for chelating the metal ion as well as being a good donor for example as disclosed in European Patent Application No. 0,195,413.

It may be advantageous to include a synergist to stabilize and augment the lanthanide ion fluorescence, for example trioctylphosphine oxide or other known synergist. It may also be desirable for the contacting to be carried out at a suitably elevated temperature to speed up the formation of a detectable quantity of the condensation product, for example, it could be carried out as a post-column treatment of the sample in HPLC.

Such a detection method enjoys the sensitivity associated with lanthanide ion fluorescence, especially when time-resolution principles are used to achieve specificity. The absorption maximum of the dihydropyridine condensation product should of course be different from that of the β-diketone starting material, otherwise a separation step might be required.

An example of an improved amine detection system would include contacting an unknown solution with a β-diketone and an aldehyde chelated to lanthanide metal ion. The detection of fluorescence at the excitation maximum of the dihydropyridine condensation product as illustrated in FIG. 7 indicates the presence of an amine.

An example of an improved aldehyde detection system would operate on the same principles as the amine detection system described above with the exception that the aldehyde reactant is replaced with an amine carrying a lanthanide metal ion by chelation.

The invention is further illustrated by the following nonlimiting examples:

EXAMPLE 1

Different wavelength-shifting devices were placed in front of a silicon-photovoltaic cell which was then exposed to sunlight. The electrical output from the photovoltaic cell wa measured in volts produced across an electric motor. The results of this experiment are shown below in Table 1. The degree to which the fluorophore enhanced the photovoltaic cell is recorded in terms of percent. The silicon-photovoltaic cell was a Radio Shack model numbered 277-1201. Each wavelength-shifting device included a polystyrene film base. Some of the devices also included coatings of the various fluorophores described in this paper. The dihydropyridine condensation product is denoted as DHP in Table 1.

TABLE 1

| Configuration | Voltage Across Motor | % Increase |
|---|---|---|
| Plain film | 0.411 | — |
| Film with DHP $Tb^{3+}$ | 0.422 | 2.68 |
| Film with DHP $Eu^{3+}$ | 0.445 | 8.27 |

EXAMPLE 2

This is an example of an amine detection system. Proteins are characterized by their amine tails. The concentration of proteins in a solution was determined by measuring the Eu(III) ion fluorescence associated with the dihydropyridine condensation product. The Eu(III) ion fluoresces at the new excitation wavelength introduced by product formation. The materials used in this example are as follows:

| | |
|---|---|
| TBA-TFA | $0.5 \times 10^{-3}$M in a 0.1M acetate buffer at pH 5.5 |
| Chelating aldehyde | $0.37 \times 10^{-3}$M in a 0.1M acetate buffer at pH 5.5 |
| Antibody solution | Serially diluted in a 0.1M acetate buffer at pH 5.5 |

The procedure used in this example is as follows: 0.5 ml each of aldehyde (with Eu) and β-diketone solution were added to 1 ml aliquots of different known concentrations of antibody. The solutions were incubated for one hour at 37° C. and cooled to room temperature. Fluorescence was measured in a Perkin Elmer LS5 spectrofluorometer under a delayed fluorescence mode with the following settings:
Delay 0.05 ms
Gate 0.5 ms
Fixed scale 2.0
Slits Ex 15; Em 20; Ex 277 nm Em 615 nm
The results from this example are shown below in Table 2.

TABLE 2

| Protein Concentration (mg/ml) | M | Fluorescence |
|---|---|---|
| 0.87 | $5.7 \times 10^{-6}$ | 68 |
| 0.22 | $1.4 \times 10^{-6}$ | 18 |
| 0.05 | 0.36 | 9 |
| 0 | | 4 |

The same samples were photon counted using a time-gated fluorometer after separation of small molecules. The counts measured are recorded in Table 3. The data in Table 3 was used to construct a calibration curve for determining unknown protein concentrations by interpolation.

TABLE 3

| Protein Concentration (mg/ml) | Counts |
|---|---|
| 0.87 | $2.2 \times 10^8$ |
| 0.22 | $5.5 \times 10^7$ |
| 0.05 | $1.4 \times 10^7$ |
| 0.01 | $3.0 \times 10^6$ |
| 0.003 | $8.6 \times 10^5$ |
| 0 | $2.0 \times 10^3$ |

EXAMPLE 3

This is an example of an aldehyde detection system. The concentration of formaldehyde, an aldehyde, in a solution was determined by method of the condensation product formation together with delayed-timegated Eu(III) flourescence measurements similar to Example 2.
The materials used in this example are as follows:

1. A $1 \times 10^{-3}$M concentration of β-diketone (TBA-TFA) containing a stoichiometric amount of Eu(III) in a 0.1M acetate buffer at pH 5.5
2. A 2.0M concentration of amine - ammonium acetate in a 0.1M acetate buffer at pH 5.5
3. Formaldehyde solutions diluted in a 0.1M acetate buffer at pH 5.5

The stock solution consisted of a β-diketone solution mixed with ammonium acetate solution in a 1:1 ratio. The procedure used in this example is as follows:
1 ml of the mixed stock solution of β-diketone and ammonium acetate were added to 1 ml aliquots of diluted formaldehyde solutions. The solutions were incubated for 1 hour at 37° C. and cooled to room temperature. The fluorescence of the solution was measured in a Perkin Elmer Spectrofluormometer without separation.

The results from this example are as follows: The excitation spectrum did not have two peaks. It had the identical peak corresponding to the β-diketone. The peak at 280 nm in the case of the antibody product is attributed to the antibody. The signal detector was necessary to eliminate noise from the unreacted β-diketone-Eu(III) complex. The readings therefore decreased with increasing concentration as shown below in Table 4. A calibration curve, similar to that constructed in example 2, could be used to determine the formaldehyde concentrations.

TABLE 4

| Formaldehyde Concentration (M) | Reading Ex 350 Em 615 Scale Factor | Counts |
|---|---|---|
| $10^{-3}$ | 168 | $8.6 \times 10^6$ |
| $10^{-4}$ | 61 | $3.2 \times 10^8$ |
| $10^{-5}$ | 204 | $3.8 \times 10^9$ |
| $10^{-6}$ | 251 | $4.4 \times 10^9$ |
| $10^{-7}$ | 256 | $4.5 \times 10^9$ |
| blank | 266 | $4.6 \times 10^9$ |

The invention may be embodied in other specific forms without departing from the spirit or essential characteristics thereof. The present embodiments are therefore to be considered in all respects as illustrative and not restrictive, the scope of the invention being indicated by the appended claims rather than by the foregoing description, and there is no intention to exclude any equivalence thereof. Hence, it is recognized that various modifications are possible when within the scope of the present invention as

What is claimed is:

1. A method for detecting the amount of amine present in a sample comprising contacting a sample with a lanthanide metal ion, a β-diketone, and an aldehyde such that the β-diketone and the aldehyde react with any amine present in the sample to produce a dihydrophyridine condensation reaction product which then chelates the lanthanide metal ion and then measuring long lived fluorescence of any chelated metal ion to determine the amount of amine present in the sample.

2. The method as set forth in claim 1, wherein long lived fluorescence is measured with a fluorometer.

3. A method for detecting the amount of aldehyde present in a sample comprising contacting a sample with a lanthanide metal ion, a β-diketone, and an amine such that the β-diketone and the amine react with any aldehyde present in the samples to produce a dihydropyridine condensation reaction product which then chelates the lanthanide metal ion and then measuring long lived flurorescence of any chelated metal ion to determine the amount of aldehyde present in the sample.

4. The method as set forth in claim 3, wherein long lived fluorescence is measured with a fluorometer.

* * * * *